United States Patent [19]

Yardley et al.

[11] 4,338,173

[45] Jul. 6, 1982

[54] CATALYTIC ISOMERIZATION PROCESS USING PHOTO-INDUCED DELIGANDATION

[75] Inventors: James T. Yardley, Morristown; Alan M. Rosan, Madison; Eva L. Menger-Hammond, Madison, all of N.J.

[73] Assignee: Allied Corporation, Morris Township, Morris County, N.J.

[21] Appl. No.: 161,998

[22] Filed: Jun. 23, 1980

[51] Int. Cl.$^3$ ................................................ C07C 5/23
[52] U.S. Cl. .................... 204/162 R; 204/162 HE; 585/665; 585/670
[58] Field of Search ................. 204/162 R, 162 HE; 585/664, 665, 667, 668, 669, 670, 671

[56] References Cited

U.S. PATENT DOCUMENTS

| | | | |
|---|---|---|---|
| 2,914,452 | 11/1959 | Schultze | 204/162 HE |
| 3,158,559 | 11/1964 | Caffrey | 204/162 HE |
| 3,158,560 | 11/1964 | Caffrey | 204/162 HE |
| 3,248,313 | 4/1966 | Crain | 204/162 HE |
| 3,439,054 | 4/1969 | Kroll | 585/670 |
| 3,634,540 | 1/1972 | Wang | 585/670 |
| 3,793,257 | 2/1974 | Pennella | 585/670 |
| 3,954,821 | 5/1976 | Herskovitz | 585/670 |
| 4,087,472 | 5/1978 | Hughes | 585/667 |

*Primary Examiner*—Paul R. Michl
*Attorney, Agent, or Firm*—James Riesenfeld

[57] ABSTRACT

A process is provided for inducing a catalytic isomerization reaction. The process involves exposing to optical radiation a gaseous mixture including a reactant unsaturated hydrocarbon and a compound of a transition metal and a ligand. The gaseous transition metal compound is preferably a transition metal carbonyl.

19 Claims, No Drawings

CATALYTIC ISOMERIZATION PROCESS USING PHOTO-INDUCED DELIGANDATION

DESCRIPTION

BACKGROUND OF THE INVENTION

1. Field of the Invention

This invention relates to a homogeneous catalysis process that employs as a catalyst a gaseous transition metal compound subjected to photo-induced deligandation.

2. Description of the Prior Art

A known method of preparing catalysts is by deligandation; i.e., the removal of one or more ligands, of compounds of transition metals and ligands. Deligandation has generally been accomplished either thermally or photochemically in solution.

Thermal deligandation of a compound of the form $ML_n$, where M is a transition metal and L is a ligand, generally results in the production of a mixture of species ($ML_{n-1}$, $ML_{n-2}$, ... ) in which the more highly active species are relatively minor constituents. Although removal of a single ligand and complete removal of ligands have been reported, the removal of a specified number of ligands (more than one) cannot in general be accomplished thermally.

Photochemical deligandation, particularly of transition metal carbonyls, has been the subject of a great deal of study and has been summarized recently in G. L. Geoffroy and M. S. Wrighton, *Organometallic Photochemistry* (Academic Press, New York, 1979), Chapter 2. Dissociative loss of one or more CO groups yields one or more coordinatively unsaturated intermediates. In general, the photo reactions have been accomplished with the transition metal carbonyl compounds either in an inert liquid solvent (see, e.g., M. Wrighton, Chem. Rev. 74, 401 (1974)) or matrix-isolated; i.e., trapped in an inert rigid matrix, usually a solid noble gas at low temperatures (see, e.g., J. J. Turner et al., Pure and Appl. Chem. 49, 271 (1977)).

Photochemical treatment of transition metal carbonyls in solution generally results in loss of only the single ligand that is most weakly bound, while irradiation of matrix-isolated carbonyls requires high input energy and yields a deligandated product in a frozen form, of limited direct utility.

Photolysis of metal carbonyls in the gaseous phase has been reported by Z. Karny et al., Chem. Phys. Lett. 59, 33 (1978) and by L. Hellner et al., Nouveau Journal De Chimie 3, 721 (1979). Karny et al. produced electronically excited metal atoms by focusing on the gas the output of an ArF (193 nm) or KrF (249 nm) laser. The fluence incident on the gas was extremely high. The production of excited metal atoms was postulated to occur by a multiphoton mechanism in which the net yield of excited metal atoms depends on the square of the radiation intensity. Hellner et al., on the other hand, used rather low fluence from conventional rare gas lamps. While Karny et al. gave no indication that partial deligandation results from their procedure, Hellner et al. specifically concluded that their process involves direct dissociation to an electronically excited metal atom without generating any intermediate products. The resultant excited metal atom is generally not a good catalyst.

Transition metal compounds, including carbonyls, have been studied as photocatalysts and photoassistance agents (M. S. Wrighton et al. Pure and Appl. Chem. 41, 671 (1975)). Photolysis of $W(CO)_6$, $Mo(CO)_6$, $Cr(CO)_6$ and $Fe(CO)_5$ in liquid solvents leads to the generation of intermediates that assist or catalyze olefin reactions, including isomerization.

SUMMARY OF THE INVENTION

In accordance with the present invention, a process is provided for inducing a catalytic isomerization reaction in a reactant gas comprising an unsaturated hydrocarbon, which comprises exposing the gas to optical radiation in the presence of a gaseous compound comprising a transition metal and a ligand.

The catalytic reactions of this invention are useful for preparing reagents for organic synthesis, including isomers that are much more difficult to prepare by the processes of the prior art.

Optical radiation in the context of the specification and claims refers to electromagnetic radiation in the range from ultraviolet to infrared, with wavelengths from about 150 nm to 2000 nm.

DETAILED DESCRIPTION OF THE INVENTION

By exposing to optical radiation a mixture comprising a gaseous unsaturated hydrocarbon and a gaseous compound comprising a transition metal and a ligand, the gaseous hydrocarbon is made to undergo a catalytic isomerization reaction. Such a reaction may be represented by the equation:

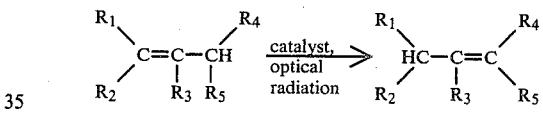

wherein the $R_1$ through $R_5$ groups are independently selected from the group consisting of hydrogen, hydroxyl; alkyl, straight chain, branched or cyclic, having 1 to 7 carbon atoms, and optionally substituted by halogen or nitrile; alkenyl, mono- and di-unsaturated, straight chain or branched, having 1 to 7 carbon atoms; alkynyl, mono- and di-substituted, having 1 to 7 carbon atoms; and phenyl and substituted phenyls, having 7 or fewer carbon atoms. Any two $R_1$–$R_5$, when taken together, may be alkylene groups having a cyclo-aliphatic structure.

Exemplary organic $R_1$ through $R_5$ groups include methyl, ethyl, n-propyl, i-propyl, n-butyl, i-butyl, sec-butyl, t-butyl, vinyl, hydroxyl, phenyl, allenyl, cyclopropyl, cyclobutyl, cyclobutenyl, cyclopentenyl, ethynyl, 1-propynyl, 2-propynyl, 1-butynyl, 2-butynyl, and 3-butynyl. Other suitable hydrocarbons include cyclic compounds obtained from linkages between R's; for example, $R_1$–$R_2$, $R_2$–$R_3$, $R_3$–$R_4$, $R_4$–$R_5$, and $R_1$–$R_4$. Preferably, the total number of carbon atoms does not exceed 10. Olefins, such as 1,4-pentadiene, are particularly suitable.

The ligand(s) of the transition metal compound, whch may be the same or different, are independently selected from the group consisting of hydrogen, halogen, nitrile; isonitrile, having 1–4 carbon atoms and optionally substituted by halogen; alkyl, straight chain or branched, having 1–4 carbon atoms and optionally substituted by halogen; alkoxy, having 1–4 carbon atoms and optionally substituted by halogen; mono- and di-unsaturated olefins, internal or terminal, having 1–4 carbon atoms and optionally substituted by halogen;

cyclic di- and tri-olefins, having 1–7 carbon atoms; phenyl, optionally substituted by halogen; allyl, trifluorophosphine, carbon monoxide, ammonia, nitric oxide, and nitrogen.

Exemplary organic ligands of the transition metal compound include methyl, ethyl, n-propyl, i-propyl, tert-butyl, n-butyl, i-butyl, sec-butyl, methoxy, ethoxy, n-propoxy, ethylene, propylene, 1-butylene, 2-butylene, butadiene, allyl, cyclopentadienyl, cyclobutadiene, 1,3-cyclohexadiene, 1,4-cyclohexadiene; $C_6R_6$, where each R is independently selected from the group consisting of hydrogen, methyl, and fluorine; tetrafluoroethylene, perfluoropropylene, perfluoromethyl, perfluoroethyl, perfluoropropyl, perfluorobutyl, tetrafluoroethyl, vinyl, ethynyl, and combinations thereof. To facilitate photolysis, the ligand to be removed by the optical radiation is bound to the transition metal by a bond energy that is preferably less than about 400 kJ/mole and more preferably less than about 200 kJ/mole. Preferably, the ligand is CO, NO or combinations thereof; more preferably, CO. Among transition metal carbonyls, those in which the transition metal is a group VIB or group VIII metal are preferred. Particularly suitable are $Cr(CO)_6$, $Fe(CO)_5$, and $Fe(CO)_2(NO)_2$.

Catalytic sites are provided by photodeligandation of the transition metal compound, which generates coordinatively unsaturated intermediates. An important characteristic of the present process is that a large proportion of the intermediates has lost more than one ligand and are, consequently, particularly active.

The product of the catalytic reaction may be separated and recovered by conventional processes well known in the art, such as fractional distillation and chromatography. Since the deligandated transition metal compound is the catalyst, it is regenerated during the catalytic reaction. To the extent that the catalyst is deactivated, it may be formed again by photolysis of the transition metal compound.

The vapor pressure of the reactant gas should exceed about 133 Pa and preferably be in the range from about $1.3 \times 10^3$ Pa to $1.3 \times 10^6$ Pa. The transition metal compound should have a vapor pressure above about 0.13 Pa. The temperature range should be about 0° C.–100° C. Room temperature, about 25° C., is suitable and convenient. The ratio of reactant gas partial pressure to transition metal compound pressure should be in the range of about 10 to $10^{10}$, preferably about $10^3$ to $10^5$. If the ratio is too low, collisions between the photofragments and the starting transition metal compound reduce the population of multi-deligandated intermediates. If the ratio is too high, there is insufficient transition metal compound to provide efficient absorption of the radiation. Preferably, radiation should be at a wavelength, or in a wavelength range, that is strongly absorbed by the transition metal compound.

Deligandation of transition metal compounds on exposure to optical radiation may be accomplished as a single-photon process, if the photon energy exceeds the metal-ligand bond energy, or as a multiphoton process. The original compound may be represented by the formula $ML_n$ and the deligandated intermediate by $ML_{n-x}$, where M is a transition metal and L is a ligand. Preferably, n and x are each greater than 1 and $(n-x) \geq 1$. This multi-deligandation is best accomplished by using radiation whose photon energy is at least twice, and preferably at least three times, the metal-ligand bond dissociation energy. Ultraviolet radiation of wavelength in the range from about 150 nm to 400 nm is preferred.

In general, on exposure to ultraviolet radiation, more than one deligandated intermediate of the compound is formed, each having a different value of x. The relative amounts of the various intermediates are determined by the values of the process parameters, such as the partial pressures of reactant gas and transition metal compound and the wavelength, intensity, fluence, and number of pulses of the optical radiation. Although the relationship between product distribution and process parameters is not simple, routine experimentation provides the parameters that maximize the yield of the particular intermediate desired.

It is desirable to minimize the effects of photolysis of photofragments or intermediates generated from the transition metal compound. Thus, pulsed light sources are preferred, with fluence preferably chosen so that the probability of a molecule of the transition metal compound absorbing more than one photon from a single pulse is substantially less than one. Typically, this requirement is met when the fluence is less than about 50 mJ/cm². For the same reason, the interval between pulses is preferably long compared with the time for diffusion out of the irradiated volume. If the reactants are made to flow continuously through the irradiated volume, then higher pulse repetition rates may be used, providing desirably higher throughput. Typically, pulse durations about $10^{-8}$ s or less are preferred for reactant gas pressures of about $1.3 \times 10^4$ Pa. Repetition rates below 10 Hz, and typically about 1 Hz, are preferred when the gas is not flowing through the irradiated volume. For convenience, even lower repetition rates may be used, but they are not preferred for a practical system.

A continuous source may also be used. In that case, the intensity is preferably chosen so that the probability of a fragment or intermediate absorbing a photon is substantially less than one.

A laser may provide the optical radiation for the process of this invention. An unfocused KrF laser is a particularly suitable source. Since conventional light sources are generally less expensive, however, a mercury arc lamp or other incoherent source may be used when cost is an important consideration.

In order to more fully illustrate the present invention and the manner of practicing it, the following examples are presented. The examples are not to be construed as limiting the scope of the invention.

EXAMPLE 1

At room temperature, a gaseous mixture of 1,4-pentadiene and $Cr(CO)_6$ at partial pressures of $3.6 \times 10^4$ Pa and 2.7 Pa, respectively, is placed in a stainless steel cell, 38 mm in diameter by 100 mm long, having quartz windows. The mixture is irradiated with 200 pulses from a KrF laser (248 nm, pulse duration = 10 ns, energy = 10 mJ, fluence = 10 mJ/cm²) at thirty-second intervals. The resultant products, trans-1,3-pentadiene and cis-1,3-pentadiene, are identified by gas chromatography. From the known absorption coefficient ($2.4 \times 10^{-3}$ cm$^{-1}$Pa$^{-1}$), the net yields of products per absorbed photon are determined.

EXAMPLE 2

The procedure of Example 1 is repeated using $Fe(CO)_5$ at a pressure of 2 Pa in place of $Cr(CO)_6$. The partial pressure of 1,4-pentadiene is $2.7 \times 10^3$ Pa. The 1,4-pentadiene is isomerized to 1,3-pentadiene.

We claim:

1. A process for inducing a catalytic isomerization reaction in a reactant gas comprising an unsaturated hydrocarbon, which comprises exposing the gas to optical radiation in the presence of a gaseous compound comprising a transition metal and a ligand.

2. The process of claim 1 wherein the unsaturated hydrocarbon has the formula:

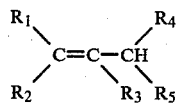

wherein the $R_1$ through $R_5$ groups are independently selected from the group consisting of hydrogen, hydroxyl; alkyl, straight chain, branched or cyclic, having 1 to 7 carbon atoms, and optionally substituted by halogen or nitrile; alkenyl, mono- and di-unsaturated, straight chain or branched, having 1 to 7 carbon atoms; alkynyl, mono- and di-substituted, having 1-7 carbon atoms; and phenyl and substituted phenyls, having 7 or fewer carbon atoms.

3. The process of claim 2 wherein the unsaturated hydrocarbon is an olefin.

4. The process of claim 2 wherein the unsaturated hydrocarbon is 1,4-pentadiene.

5. The process of claim 1 wherein the transition metal is bound to the ligand with a bond energy less than about 400 kJ/mole.

6. The process of claim 5 wherein the transition metal is bound to the ligand with a bond energy less than about 200 kJ/mole.

7. The process of claim 1 wherein the ligand is selected from the group consisting of hydrogen, halogen, nitrile; isonitrile, having 1-4 carbon atoms and optionally substituted by halogen; alkyl, straight chain or branched, having 1-4 carbon atoms and optionally substituted by halogen; alkoxy, having 1-4 carbon atoms and optionally substituted by halogen; mono- and di-unsaturated olefins, internal or terminal, having 1-4 carbon atoms and optionally substituted by halogen; cyclic di- and tri-olefins, having 1-7 carbon atoms; phenyl, optionally substituted by halogen; allyl, trifluorophosphine, carbon monoxide, ammonia, nitric oxide, nitrogen, and combinations thereof.

8. The process of claim 7 wherein the ligand is CO.

9. The process of claim 1 wherein the transition metal is selected from the group consisting of group VIB and group VIII metals.

10. The process of claim 9 wherein the gaseous compound is $Cr(CO)_6$.

11. The process of claim 9 wherein the gaseous compound is $Fe(CO)_5$.

12. The process of claim 1 wherein the optical radiation is provided by a pulsed source.

13. The process of claim 12 wherein the radiation fluence is chosen so that the probability of a molecule of the transition metal compound absorbing more than one photon from a single pulse is substantially less than one.

14. The process of claim 1 wherein the optical radiation is provided by a continuous source.

15. The process of claim 14 wherein the radiation intensity is chosen so that the probability of a fragment or intermediate generated from the transition metal compound absorbing a photon is substantially less than one.

16. The process of claim 1 wherein the optical radiation is in the ultraviolet region of the electromagnetic spectrum.

17. The process of claim 16 wherein the optical radiation is provided by a mercury arc lamp.

18. The process of claim 1 wherein the optical radiation is provided by a laser.

19. The process of claim 18 wherein the optical radiation is provided by a KrF laser.

* * * * *